(12) United States Patent
Baron et al.

(10) Patent No.: US 11,957,448 B2
(45) Date of Patent: *Apr. 16, 2024

(54) DIAGNOSTIC TOOL AND METHOD OF USE

(71) Applicant: spirox, inc., Menlo Park, CA (US)

(72) Inventors: Scott J. Baron, Plymouth, MN (US);
Michael H. Rosenthal, Plymouth, MN (US)

(73) Assignee: Spirox, Inc., Menlo Park, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/130,651

(22) Filed: Apr. 4, 2023

(65) Prior Publication Data
US 2023/0233100 A1 Jul. 27, 2023

Related U.S. Application Data

(63) Continuation of application No. 17/214,872, filed on Mar. 28, 2021, now Pat. No. 11,642,043, which is a
(Continued)

(51) Int. Cl.
*A61B 5/087* (2006.01)
*A61B 1/00* (2006.01)
(Continued)

(52) U.S. Cl.
CPC .......... *A61B 5/087* (2013.01); *A61B 1/00147* (2013.01); *A61B 1/233* (2013.01);
(Continued)

(58) Field of Classification Search
CPC ....... A61B 1/00147; A61B 1/04; A61B 1/233; A61B 5/087; A61B 5/091; A61B 5/097;
(Continued)

(56) References Cited

U.S. PATENT DOCUMENTS 10,987,024 B2 * 4/2021 Baron ................ A61B 1/00147
11,642,043 B2 * 5/2023 Baron ................ A61B 1/00147
382/128
(Continued)

FOREIGN PATENT DOCUMENTS

CN          2566251       8/2003
WO     2016007749 A2     1/2016

OTHER PUBLICATIONS

PCT International Search Report for PCT/US2017/051827, Applicant: Spirox, Inc., Form PCT/ISA/210 and 220, dated Jan. 23, 2018 (5pages).
(Continued)

*Primary Examiner* — Michael J Vanchy, Jr.
(74) *Attorney, Agent, or Firm* — McDonnell Boehnen Hulbert & Berghoff LLP

(57) ABSTRACT

A diagnostic tool and methods of using the tool are provided to quantify an amount of nasal collapse in a patient. The diagnostic tool includes a mask with an endoscope port and an opening to allow air flow, an endoscope with a camera adapted to take an image of the nasal valve, and an air flow sensor adapted to measure an inhalation rate of the patient. The diagnostic tool can quantify a size difference between
(Continued)

the nasal valve during inhalation and zero flow by calculating a percentage difference in an area or one or more dimensions of the nasal valve during inhalation and zero flow.

20 Claims, 14 Drawing Sheets

Related U.S. Application Data continuation of application No. 16/331,946, filed as application No. PCT/US2017/051827 on Sep. 15, 2017, now Pat. No. 10,987,024.

(60) Provisional application No. 62/395,936, filed on Sep. 16, 2016.

(51) Int. Cl.
| | |
|---|---|
| A61B 1/233 | (2006.01) |
| A61B 5/00 | (2006.01) |
| A61B 5/091 | (2006.01) |
| A61B 5/097 | (2006.01) |
| A61B 5/107 | (2006.01) |
| A61B 5/11 | (2006.01) |
| A61M 16/06 | (2006.01) |
| A61M 16/00 | (2006.01) |

(52) U.S. Cl.
CPC .............. *A61B 5/091* (2013.01); *A61B 5/097* (2013.01); *A61B 5/1076* (2013.01); *A61B 5/1128* (2013.01); *A61B 5/743* (2013.01); *A61M 16/0666* (2013.01); *A61M 2016/0039* (2013.01); *A61M 16/06* (2013.01)

(58) Field of Classification Search
CPC ..... A61B 5/1076; A61B 5/1128; A61B 5/743; A61M 16/06; A61M 16/0666; A61M 2016/0039
See application file for complete search history.

(56) References Cited

U.S. PATENT DOCUMENTS

| | | |
|---|---|---|
| 2001/0000346 A1 | 4/2001 | Raton et al. |
| 2006/0185680 A1 | 8/2006 | Bhat et al. |
| 2013/0096382 A1 | 4/2013 | Alexander et al. |
| 2013/0197303 A1 | 8/2013 | Chun |
| 2013/0327333 A1 | 12/2013 | Ng et al. |
| 2015/0051449 A1* | 2/2015 | Qiu ..................... A61B 5/0836 600/407 |
| 2015/0327806 A1 | 11/2015 | Kezirian et al. |

OTHER PUBLICATIONS

PCT Written Opinion of the International Search Authority for PCT/US2017/051827, Applicant: Spirox, Inc., Form PCT/SA/237, dated Jan. 23, 2018 (7pages).
Barham et al., Two-dimensional assessment of the nasal valve area cannot predict minimum cross sectional area or airflow resistance, In: American journal of rhinology & allegy, May 2016 [online] [retrieved on Jan. 3, 2018 Jan. 3, 2018)] Retrieved from the Internet <URL:https:/lwww.ncbi.nlm.nih.gov/pubmed/27216349>.
PCT International Preliminary Report on Patentability (Chapter I of the Patent Cooperation Treaty) for PCT/US2017/051827, Applicant: Spirox, Inc., Form PCT/IB/326 and 373, dated Mar. 28, 2019 (9pages).
Bhatia DDS, Palesy T, Ramli R, et al. Two-dimensional Assessment of the Nasal Valve Area Cannot Predict Minimum Cross-Sectional Area or Airflow Resistance. American Journal of Rhinology & Allergy. 2016;30(3): 190-194. First Published May 1, 2016 (Year: 2016).
English Translation of Abstract of Chinese Patent Application No. 2566251 dated Mar. 3, 2022.
Tsao, Gabriel J. et al., "Validation of a grading system for lateral nasal wall insufficiency", Allergy & Rhinology, Fall 2013, vol. 4, No. 2 pp. e66-e68.

* cited by examiner

| Grade | Percent closure of lateral wall towards the septum |
|---|---|
| 1 | <33% |
| 2 | 33-66% |
| 3 | >66% |

DIAGNOSTIC TOOL AND METHOD OF USE

CROSS REFERENCE TO RELATED APPLICATIONS

This application is a continuation of U.S. patent application Ser. No. 17/214,872, filed Mar. 28, 2021, which is a continuation of U.S. patent application Ser. No. 16/331,946, filed Mar. 7, 2019 (now U.S. Pat. No. 10,987,024), which is a U.S. National Stage filing under 35 U.S.C. § 371 of International Application No. PCT/US2017/051827, filed Sep. 15, 2017, which claims priority to U.S. Patent Application No. 62/395,936 filed Sep. 16, 2016 titled "Diagnostic Tool and Methods of Use", the contents of which are incorporated herein by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

The present disclosure relates generally to observing and treating nasal obstruction, such as nasal valve collapse.

BACKGROUND

Nasal obstruction is typically assessed via a qualitative quality of life questionnaire called the NOSE questionnaire (Nasal Obstruction Symptom Evaluation). Nasal obstruction has three primary contributors: septal deviation, turbinate hypertrophy, and constriction of the nasal valve. Nasal valve collapse is a dynamic constriction of the nasal valve due to the negative pressure generated during inspiration. Septal deviation and turbinate hypertrophy can be diagnosed endoscopically and are frequently treated surgically by ENT physicians.

Nasal valve collapse is more difficult to diagnose and severe cases are typically treated by facial plastic surgeons in substantially invasive surgical procedures relying on cartilage grafting such as Batten grafts, spreader grafts, butterfly grafts, alar strut grafts, etc. Spirox's Latera® Absorbable Nasal Implant is a polymer graft which enables treatment of nasal valve collapse in a minimally invasive manner. Examples of nasal implants are disclosed in US 2016/0058556. The nasal valve collapse treatments identified above typically function by adding stiffness to the nasal lateral wall to reduce collapse during inspiration.

It would be highly desirable to quantify the degree of nasal valve collapse before and after any surgical treatment to enable an objective assessment of the particular treatment's effectiveness in reducing collapse. There are currently no broadly accepted methods for performing this quantification of degree of valve collapse.

Several methods have been developed to quantify nasal obstruction, but these methods do not capture and sometimes mask the dynamic effects of nasal valve collapse. These methods include: acoustic rhinometry, rhinomanometry, and rhinoresistometry. These methods have been reported to have limited relevance due to their lack of correlation to patient reported subjective nasal obstruction via the NOSE score. Regardless, these methods are not designed to quantify nasal valve collapse for various reasons.

Acoustic rhinometry is a static (e.g. non-breathing) quantification of the cross sectional area of the nasal airway. As a static measurement it is inherently unable to capture the constricting effects of dynamic valve collapse. FIG. 1 illustrates an example of acoustic rhinometry including the acoustic rhinometer 10 and an example of an output 20.

Rhinomanometry relies on blocking one nostril and measuring the pressure in that closed nostril at the same time as the flow rate through the opposing nostril. This method employs a mask as well as an adhesive seal on one nostril. The result is that the mask and the tape affect the nasal lateral wall at the location of the nasal valve and significantly alter the amount of dynamic collapse confounding the measurements. In addition, data collected is often processed with the assumption of a linear relationship between pressure and flow which is not accurate if nasal valve collapse causes an anatomical self-limiting of flow at high inspiratory pressures. FIGS. 2A-2D illustrate examples of rhinomanometry devices 30, 35, 40, and 45.

Rhinoresistometry involves additional data analysis on the same pressure and flow measurements of rhinomanometry and suffers the same drawbacks related to dynamic nasal valve collapse.

One known method for quantification of nasal valve collapse (or lateral nasal wall insufficiency) is a grading system described by Tsao, Fijalkowski, and Most which utilizes direct endoscopic visualization of nasal lateral wall movement and classifies the degree of collapse as grade 0, 1, 2, or 3 based on the evaluators visual assessment of the percentage of reduction in distance between the lateral wall and the nasal septum at the location of the internal valve. FIG. 3C illustrates the Most grading scale for nasal valve collapse along with images (FIG. 3A and FIG. 3B) of the nasal valve while inhaling 55 and exhaling 50. The distance between the lateral wall and the nasal septum is shown with lines 52, 57. The length of the lines 52, 57 can be compared and classified based on the Most grading scale (FIG. 3C). There are numerous variables which limit the resolution of the Most grading system to 1-3. The most significant of these variables is the magnitude of inspiratory flow which the patient generates as the evaluation takes place. Higher inspiratory effort results in a greater negative pressure in the lungs and a higher air velocity through the constricted nasal valve which further reduces the pressure in the valve and increases collapse. Thus the degree of inspiratory effort significantly affects the magnitude of nasal valve collapse and this variable is uncontrolled.

There is currently no method for higher resolution quantification of the magnitude of nasal valve collapse. A need exists for improved systems and methods for quantifying nasal valve collapse.

SUMMARY OF THE DISCLOSURE

The present invention relates to diagnostic tools and methods of using the diagnostic tools to quantify the nasal collapse of a nasal valve of a patient.

In general, in one embodiment, methods for determining a nasal valve collapse of a patient are provided. The methods include receiving one or more images of a nasal valve of a patient taken while the patient inhales and between exhalation and inhalation, the images taken with an endoscope having a camera that passes through a port in a mask forming a seal with a facial structure of the patient; measuring an air flow rate of the patient across an opening of the mask while the patient inhales and between exhalation and inhalation; and comparing the one or more images of the nasal valve while the patient inhales and between exhalation and inhalation thereby quantifying a size difference between the nasal valve during inhalation and during a period between exhalation and inhalation.

This and other embodiments can include one or more of the following features. Quantifying the size difference between the nasal valve during inhalation and during a period between exhalation and inhalation can further include determining a first relative distance between a septum and a lateral wall of the nasal valve during inhalation; determining a second relative distance between the septum and the lateral wall of the nasal valve during the period between exhalation and inhalation; and calculating the first relative distance divided by the second relative distance to quantify the nasal valve collapse.

The methods can further include receiving one or more images of the nasal valve of the patient taken at a plurality of inhalation rates. The methods can further include determining a plurality of relative distances between the septum and the lateral wall of the nasal valve for the plurality of inhalation rates.

The methods can further include receiving an annotation of the image of the nasal valve when the patient inhales, the annotation done by a physician to indicate a distance between the septum and the lateral wall in the image of the nasal valve. The methods can further include determining a relative distance between the septum and the lateral wall based on the annotation of the image of the nasal valve when the patient inhales.

The methods can further include receiving an annotation of the image of the nasal valve during the period between exhalation and inhalation, the annotation done by a physician to indicate a distance between the septum and the lateral wall in the image of the nasal valve. The methods can further include determining a relative distance between the septum and the lateral wall based on the annotation of the image of the nasal valve during the period between exhalation and inhalation.

The methods can further include receiving a time stamp of the plurality of images of the nasal valve and the measured air flow rates. The methods can further include displaying an air flow rate at a first time and a corresponding image of the nasal valve at the first time.

The methods can further include displaying an air flow rate graph showing the air flow rate versus time. The methods can further include displaying an image of the nasal valve. The methods can further include receiving an input from a user indicating a time of interest on the air flow rate graph; and displaying a corresponding image of the nasal valve at the time of interest.

In some embodiments quantifying the size difference between the nasal valve during inhalation and the period between exhalation and inhalation can include calculating a percentage difference in an area or one or more dimensions of the nasal valve during inhalation and the period between exhalation and inhalation.

The methods can further include displaying a graph of a quantification of the nasal valve collapse at a plurality of inhalation rates versus air flow rate.

The methods can further include engaging the mask with the facial area of the patient to form a seal around the nose and the mouth of the patient to substantially seal the nose and mouth from an exterior of the mask. The methods can further include guiding the patient to a pre-determined inhalation rate. In some embodiments the one or more images include a video of the nasal valve. In some embodiments the mask does not alter a physical structure or physical properties of a nasal tissue of the patient. The methods can further include positioning the endoscope with the camera adjacent to a nasal valve of the patient.

In general, in one embodiment, methods for determining nasal valve collapse are provided. The methods can include receiving a first image of a nasal valve of a patient taken at a first time; receiving a first measurement of an airflow passing through the nasal valve of the patient at substantially the first time; determining a first relative distance between a septum and a lateral wall of the nasal valve of the patient based on the first image of the nasal valve at the first time; receiving a second image of the nasal valve of a patient at a second time different from the first time; receiving a second measurement of an airflow passing through the nasal valve of the patient at substantially the second time; determining a second relative distance between the septum and the lateral wall of the nasal valve of the patient based on the second image of the nasal valve at the second time; and comparing the first relative distance and second relative distance to provide a quantitative indication of the nasal valve collapse. In some embodiments the first time corresponds to when the patient is inhaling and the second time corresponds to a period between exhalation and inhalation. In some embodiments the first time and the second time are on a first day, wherein the first day is prior to providing a treatment to the patient.

The methods can further include receiving a first image of a nasal valve of a patient taken at a first time on a second day, wherein the second day is after the first day and a treatment provided to the patient; receiving a first measurement of an airflow passing through the nasal valve of the patient at substantially the first time on the second day; determining a first relative distance between a septum and a lateral wall of the nasal valve of the patient based on the first image of the nasal valve at the first time on the second day; receiving a second image of the nasal valve of a patient at a second time different from the first time on the second day; receiving a second measurement of an airflow passing through the nasal valve of the patient at substantially the second time on the second day; determining a second relative distance between the septum and the lateral wall of the nasal valve of the patient based on the second image of the nasal valve at the second time on the second day; and comparing the first relative distance and second relative distance to provide a quantitative indication of the nasal valve collapse on the second day. The methods can further include comparing the quantitative indication of the nasal valve collapse on the first day to the quantitative indication of the nasal valve collapse on the second day.

In some embodiments the quantitative indication of the nasal valve collapse correlates to the first relative distance divided by the second relative distance. The methods can further include displaying the quantitative indication of the nasal valve collapse and the second measurement of the air flow.

In some embodiments determining the first relative distance between the septum and the lateral wall of the nasal valve of the patient includes determining a number of pixels in an annotation provided by a physician drawing a line between the septum and the lateral wall in the first image.

In some embodiments determining the second relative distance between the septum and the lateral wall of the nasal valve of the patient includes determining a number of pixels in an annotation provided by a physician drawing a line between the septum and the lateral wall in the second image.

The methods can further include displaying an air flow rate graph showing the air flow rate versus time. The methods can further include displaying an image of the nasal valve. The methods can further include receiving an input from a user indicating a time of interest on the air flow rate graph; and displaying a corresponding image of the nasal valve at the time of interest.

The methods can further include displaying a graph of a quantitative indication of the nasal valve collapse versus air flow rate.

In general, in one embodiment systems for measuring a nasal valve collapse of a patient are provided. The systems can include a facial mask adapted to form a seal with a facial structure of the patient, the facial mask including an endoscope port and an opening to allow air flow; an air flow sensor in fluid communication with the opening of the facial mask configured to measure an air flow across the opening when the patient inhales; an endoscope with a camera adapted to pass through the endoscope port in the facial mask; and a data acquisition module adapted to receive a plurality of images from the camera and a plurality of air flow measurements from the air flow sensor. In one aspect the data acquisition module is configured to synchronize the plurality of images from the camera and the plurality of air flow measurements from the air flow sensor using a plurality of time stamps associated with the plurality of images and the plurality of air flow measurements. In some embodiments the facial mask is adapted to engage with the facial structure of the patient without changing a nasal anatomy of the patient. In some embodiments the data acquisition module is further adapted to analyze the air flow measurement, the picture of the nasal valve taken during inhalation, and the picture of the nasal valve during zero flow thereby quantifying a nasal collapse of the patient. In some embodiments quantifying the nasal collapse of the patient includes comparing the picture of the nasal valve taken during inhalation and the picture of the nasal valve during zero flow to calculate a percentage difference in an area or one or more dimensions of the nasal valve between the picture of the nasal valve taken during inhalation and the picture of the nasal valve during zero flow. In some embodiments the system is configured to perform any of the steps described herein.

In general, in one embodiment, devices for measuring a force are provided. The devices can include a plunger at a distal end of a shaft, the plunger coupled to a force gauge adapted to measure a force on the plunger, the plunger adapted to engage with an exterior surface of a lateral wall of a nose of a patient; and a displacement guide adapted to provide a visual indication of a length of a displacement of the plunger, the displacement guide including a predetermined distance. In some embodiments the displacement guide includes a ruler. In some embodiments the predetermined distance is about 5 mm or less.

In general, in one embodiment, methods are provided for measuring a property of a lateral wall of a nose of a patient. The methods can include engaging a plunger coupled to a force gauge with an exterior portion of the lateral wall of the nose; applying a force on the plunger to deflect the plunger to a predetermined distance; and recording a reading of the force gauge when the plunger is deflected to the predetermined distance. The methods can further include measuring the deflection of the plunger using a ruler on or adjacent to a portion of the plunger. In some embodiments the predetermined distance is about 5 mm or less.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
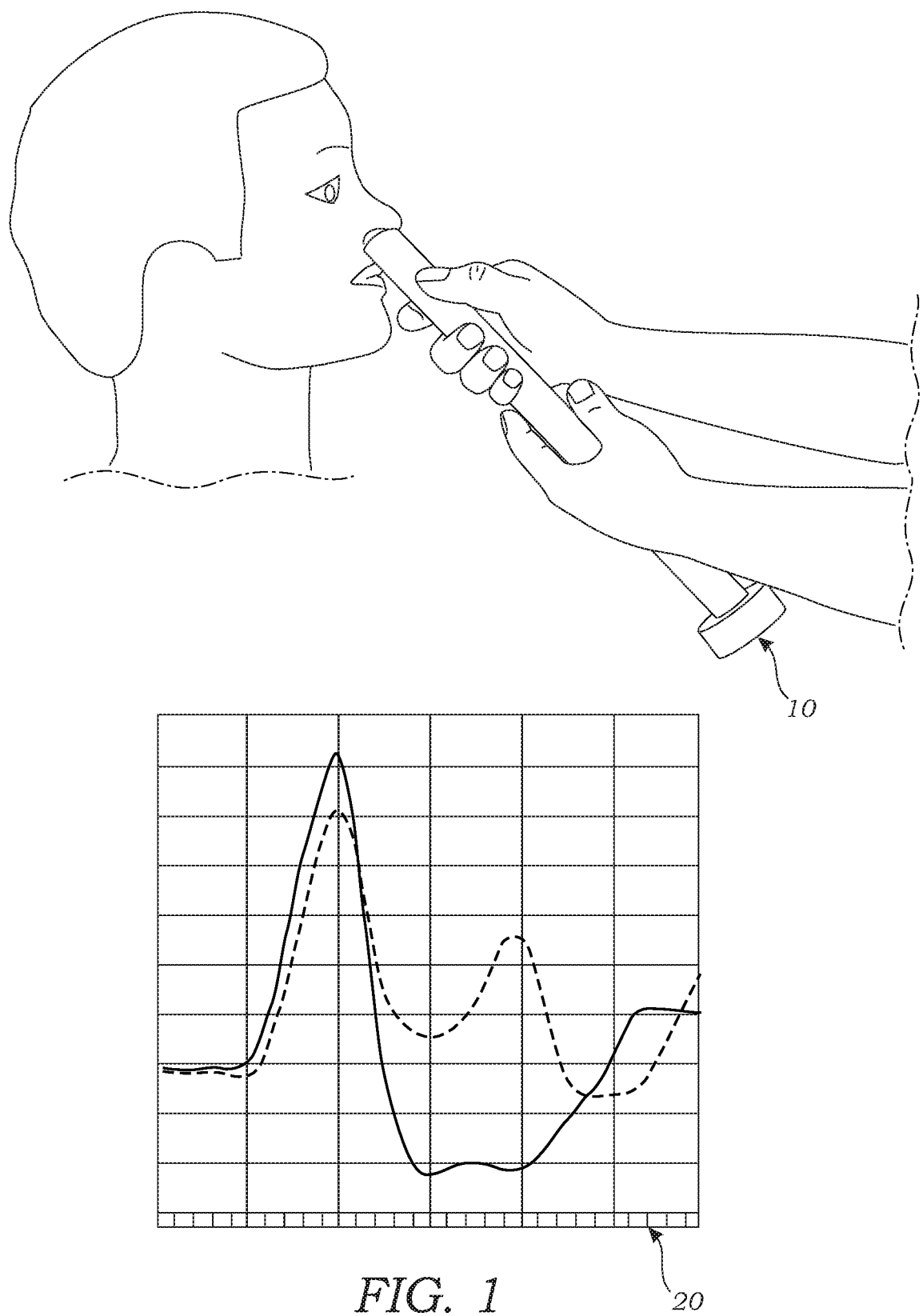
FIG. 1 is a picture of a prior art method of observing nasal obstruction.
Figure 2A:
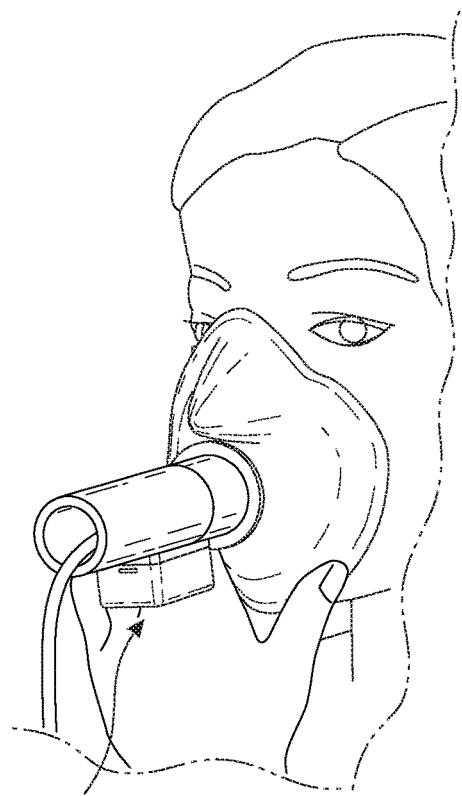
FIGS. 2A-2D illustrate another prior art technique for observing nasal obstruction.
Figure 2B:
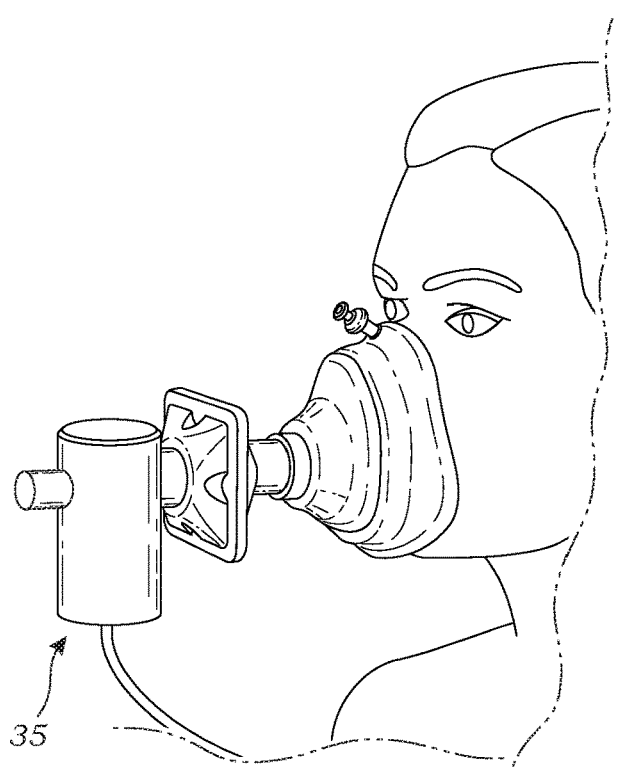
Figure 2C:
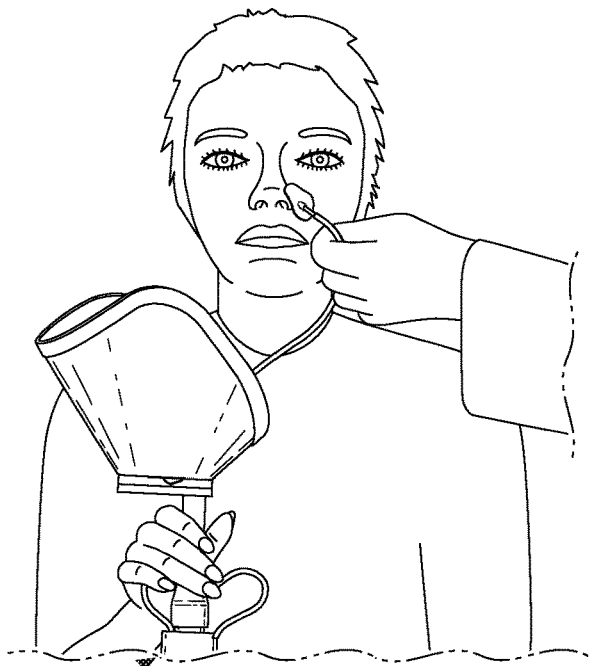
Figure 2D:
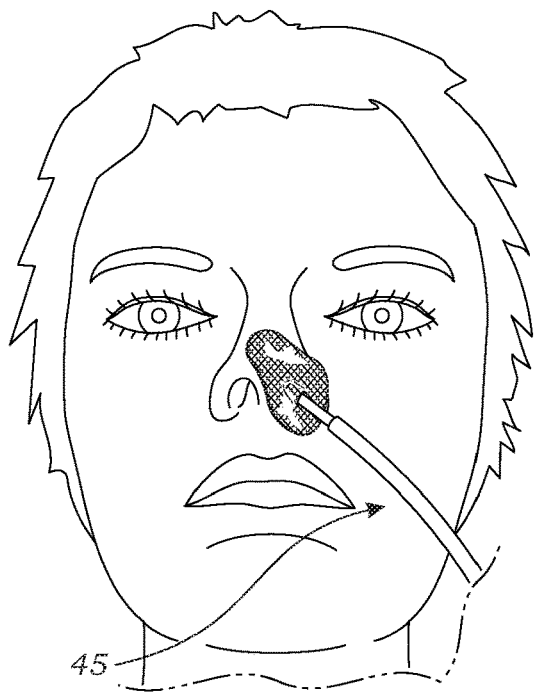
Figures 3A, 3B, 3C:
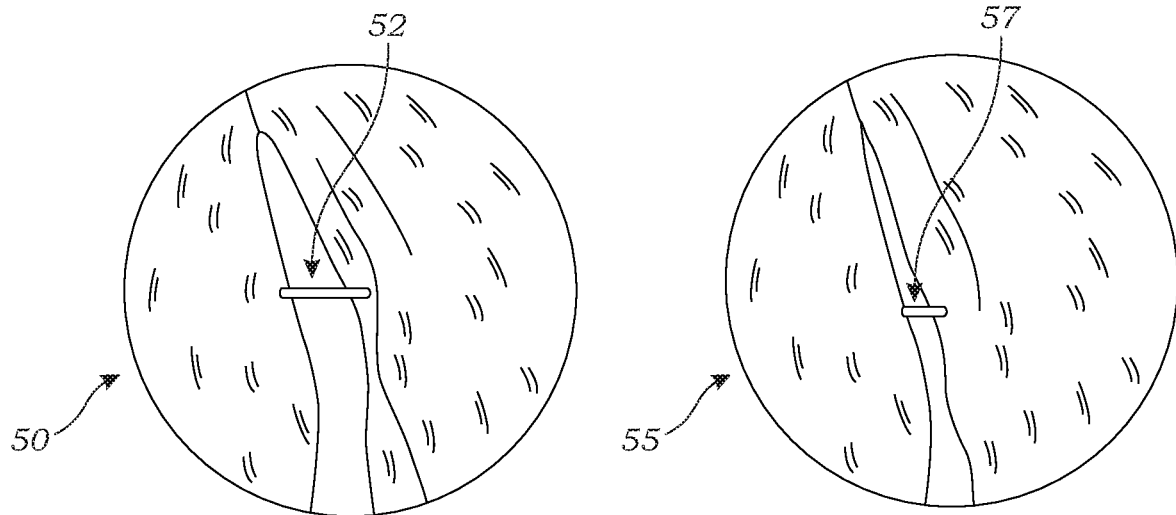
FIGS. 3A-3B illustrate images of the nasal valve during exhalation and inspiration, respectively.
FIG. 3C shows the Most grading scale for endoscopic evaluation of nasal valve collapse.

To improve resolution of the Most grading scale for nasal valve collapse, a method has been developed for capturing endoscopic visualization of lateral wall movement while simultaneously capturing nasal air flow rate without physically impeding the lateral wall movement.

The method includes the use of an airflow sensor connected to a full face mask to capture inspiratory air flow rate. The mask is designed to include a port below the nose which enables the introduction of an endoscope through a seal. Thus both airflow measurements and endoscopic video can be collected simultaneously. The method further includes software to synchronously capture both endoscopic video of lateral wall movement and air flow rate data.

Methods for determining a nasal valve collapse of a patient are provided. The methods can include: receiving one or more images of a nasal valve of a patient taken while the patient inhales and between exhalation and inhalation, the images taken with an endoscope having a camera that passes through a port in a mask forming a seal with a facial structure of the patient; measuring an air flow rate of the patient across an opening of the mask while the patient inhales and between exhalation and inhalation; and comparing the one or more images of the nasal valve while the patient inhales and between exhalation and inhalation thereby quantifying a size difference between the nasal valve during inhalation and during a period between exhalation and inhalation.

Quantifying the size difference between the nasal valve during inhalation and during a period between exhalation and inhalation can include determining a first relative distance between a septum and a lateral wall of the nasal valve during inhalation, determining a second relative distance between the septum and the lateral wall of the nasal valve during the period between exhalation and inhalation, and calculating the first relative distance divided by the second relative distance to quantify the nasal valve collapse.

In some embodiments the methods can further include receiving one or more images of the nasal valve of the patient taken at a plurality of inhalation rates. The methods can also include determining a plurality of relative distances between the septum and the lateral wall of the nasal valve for the plurality of inhalation rates.

In some embodiments the methods include receiving an annotation of the image of the nasal valve when the patient inhales, the annotation done by a physician to indicate a distance between the septum and the lateral wall in the image of the nasal valve. The methods can include determining a relative distance between the septum and the lateral wall based on the annotation of the image of the nasal valve when the patient inhales.

In some embodiments the methods include receiving an annotation of the image of the nasal valve during the period between exhalation and inhalation, the annotation done by a physician to indicate a distance between the septum and the lateral wall in the image of the nasal valve. The methods can include determining a relative distance between the septum and the lateral wall based on the annotation of the image of the nasal valve during the period between exhalation and inhalation.

In some embodiments the methods include receiving a time stamp of the plurality of images of the nasal valve and the measured air flow rates. The methods can further include displaying an air flow rate at a first time and a corresponding image of the nasal valve at the first time.

In some embodiments the methods include displaying an air flow rate graph showing the air flow rate versus time. The methods can further include displaying an image of the nasal valve. The methods can also include receiving an input from a user indicating a time of interest on the air flow rate graph and displaying a corresponding image of the nasal valve at the time of interest.

In some embodiments the methods include quantifying the size difference between the nasal valve during inhalation and the period between exhalation and inhalation includes calculating a percentage difference in an area or one or more dimensions of the nasal valve during inhalation and the period between exhalation and inhalation.

In some embodiments the methods include displaying a graph of a quantification of the nasal valve collapse at a plurality of inhalation rates versus air flow rate.

In some embodiments the methods include engaging the mask with the facial area of the patient to form a seal around the nose and the mouth of the patient to substantially seal the nose and mouth from an exterior of the mask. In some embodiments the methods include guiding the patient to a pre-determined inhalation rate. In some embodiments the methods include the one or more images include a video of the nasal valve. In some embodiments the methods include the mask does not alter a physical structure or physical properties of a nasal tissue of the patient. In some embodiments the methods include positioning the endoscope with the camera adjacent to a nasal valve of the patient.

Methods for determining nasal valve collapse are provided. In some embodiments the methods include, receiving a first image of a nasal valve of a patient taken at a first time, receiving a first measurement of an airflow passing through the nasal valve of the patient at substantially the first time, determining a first relative distance between a septum and a lateral wall of the nasal valve of the patient based on the first image of the nasal valve at the first time, receiving a second image of the nasal valve of a patient at a second time different from the first time, receiving a second measurement of an airflow passing through the nasal valve of the patient at substantially the second time, determining a second relative distance between the septum and the lateral wall of the nasal valve of the patient based on the second image of the nasal valve at the second time and comparing the first relative distance and second relative distance to provide a quantitative indication of the nasal valve collapse. In some embodiments the first time corresponds to when the patient is inhaling and the second time corresponds to a period between exhalation and inhalation.

In some embodiments the first time and the second time are on a first day, wherein the first day is prior to providing a treatment to the patient. In some embodiments the methods include receiving a first image of a nasal valve of a patient taken at a first time on a second day, wherein the second day is after the first day and a treatment provided to the patient; receiving a first measurement of an airflow passing through the nasal valve of the patient at substantially the first time on the second day; determining a first relative distance between a septum and a lateral wall of the nasal valve of the patient based on the first image of the nasal valve at the first time on the second day; receiving a second image of the nasal valve of a patient at a second time different from the first time on the second day; receiving a second measurement of an airflow passing through the nasal valve of the patient at substantially the second time on the second day; determining a second relative distance between the septum and the lateral wall of the nasal valve of the patient based on the second image of the nasal valve at the second time on the second day; and comparing the first relative distance and second relative distance to provide a quantitative indication of the nasal valve collapse on the second day. The methods can also include comparing the quantitative indication of the nasal valve collapse on the first day to the quantitative indication of the nasal valve collapse on the second day.

In some embodiments the quantitative indication of the nasal valve collapse correlates to the first relative distance divided by the second relative distance. The methods can further include displaying the quantitative indication of the nasal valve collapse and the second measurement of the air flow.

In some embodiments the methods include determining the first relative distance between the septum and the lateral wall of the nasal valve of the patient includes determining a number of pixels in an annotation provided by a physician drawing a line between the septum and the lateral wall in the first image.

In some embodiments the methods include determining the second relative distance between the septum and the lateral wall of the nasal valve of the patient includes determining a number of pixels in an annotation provided by a physician drawing a line between the septum and the lateral wall in the second image.

In some embodiments the methods include displaying an air flow rate graph showing the air flow rate versus time. The methods can also include displaying an image of the nasal valve. The methods can also include receiving an input from a user indicating a time of interest on the air flow rate graph and displaying a corresponding image of the nasal valve at the time of interest.

In some embodiments the methods include displaying a graph of a quantitative indication of the nasal valve collapse versus air flow rate.

Systems for measuring nasal valve collapse are also provided herein. In some embodiments the systems include: a facial mask adapted to form a seal with a facial structure of the patient, the facial mask including an endoscope port and an opening to allow air flow; an air flow sensor in fluid communication with the opening of the facial mask configured to measure an air flow across the opening when the patient inhales; an endoscope with a camera adapted to pass through the endoscope port in the facial mask; and a data acquisition module adapted to receive a plurality of images from the camera and a plurality of air flow measurements from the air flow sensor. The data acquisition module can be configured to synchronize the plurality of images from the camera and the plurality of air flow measurements from the air flow sensor using a plurality of time stamps associated with the plurality of images and the plurality of air flow measurements. The facial mask can be adapted to engage with the facial structure of the patient without changing a nasal anatomy of the patient.

In some embodiments the data acquisition module is further adapted to analyze the air flow measurement, the picture of the nasal valve taken during inhalation, and the picture of the nasal valve during zero flow thereby quantifying a nasal collapse of the patient. Quantifying the nasal collapse of the patient can include comparing the picture of the nasal valve taken during inhalation and the picture of the nasal valve during zero flow to calculate a percentage difference in an area or one or more dimensions of the nasal valve between the picture of the nasal valve taken during inhalation and the picture of the nasal valve during zero flow.

Devices for measuring a force are also provided. In some embodiments the devices include a plunger at a distal end of a shaft, the plunger coupled to a force gauge adapted to measure a force on the plunger, the plunger adapted to engage with an exterior surface of a lateral wall of a nose of a patient; and a displacement guide adapted to provide a visual indication of a length of a displacement of the plunger, the displacement guide including a predetermined distance. The displacement guide can includes a ruler. The predetermined distance can be about 5 mm or less.

Methods of measuring a property of a lateral wall of a nose of a patient are also provided. The methods can include engaging a plunger coupled to a force gauge with an exterior portion of the lateral wall of the nose, applying a force on the plunger to deflect the plunger to a predetermined distance, and recording a reading of the force gauge when the plunger is deflected to the predetermined distance. The methods can also include measuring the deflection of the plunger using a ruler on or adjacent to a portion of the plunger. The predetermined distance can be about 5 mm or less.

Figure 4A:
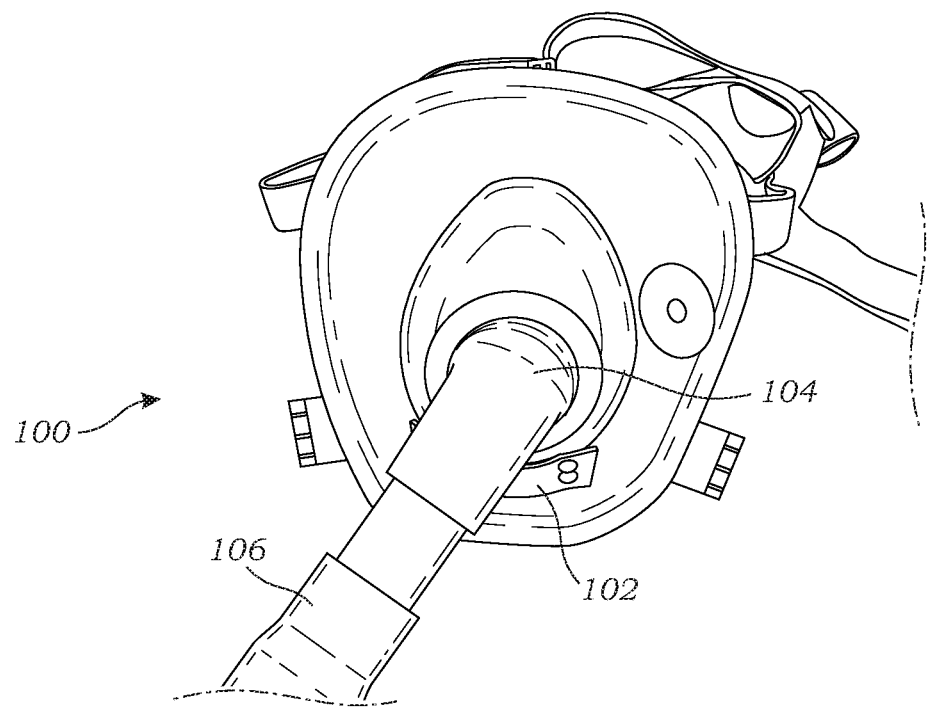
FIGS. 4A-4D illustrate a diagnostic tool for quantifying nasal valve collapse in accordance with some embodiments.
Figure 4B:
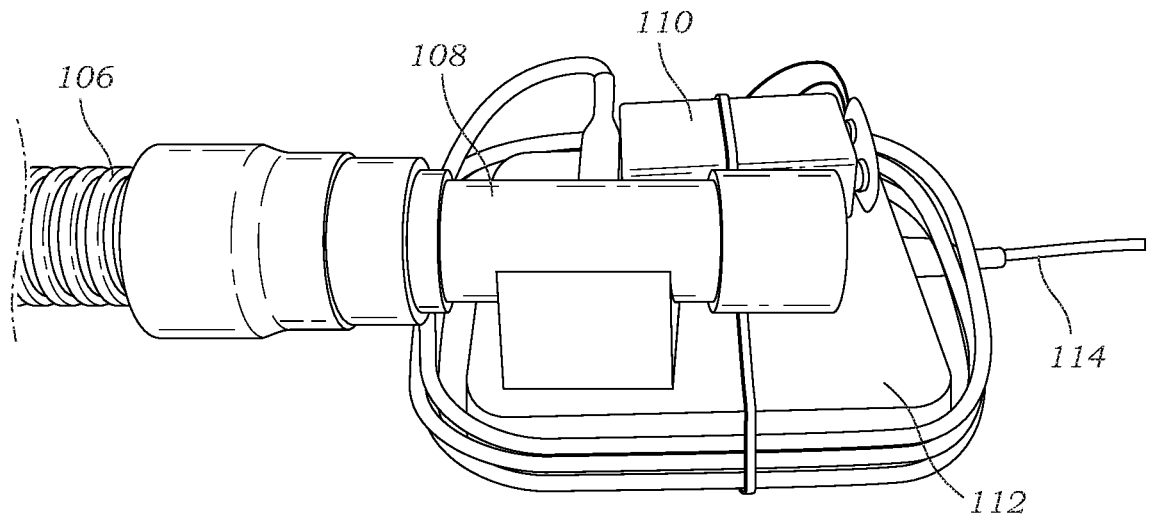
Figure 4C:
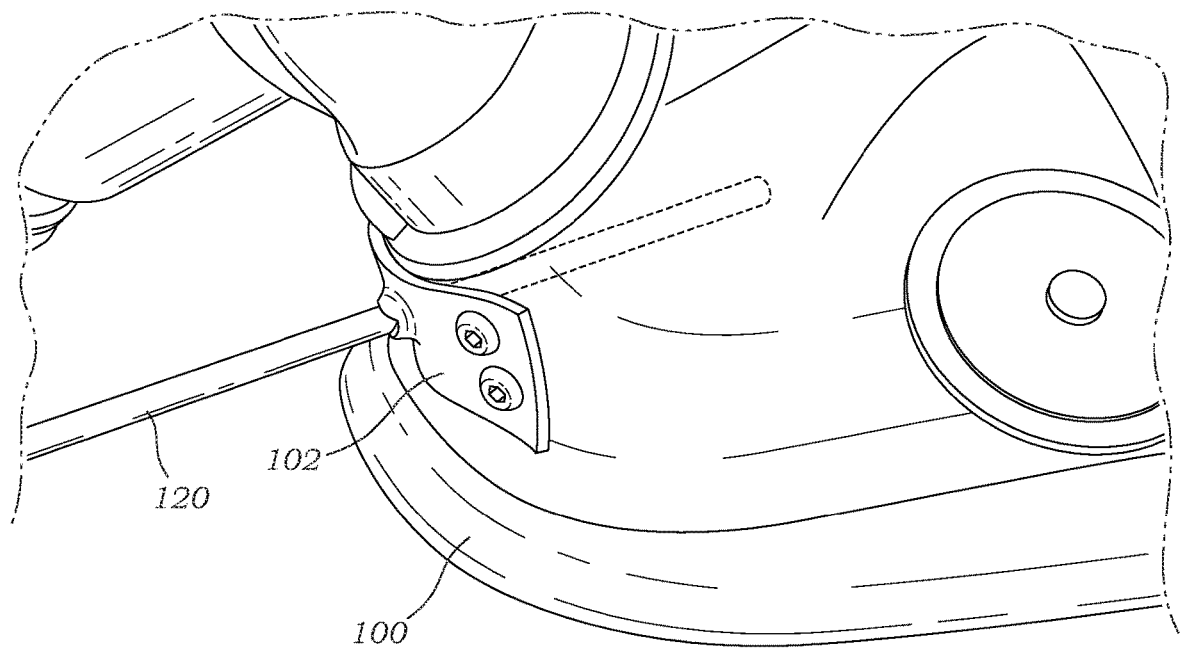
Figure 4D:
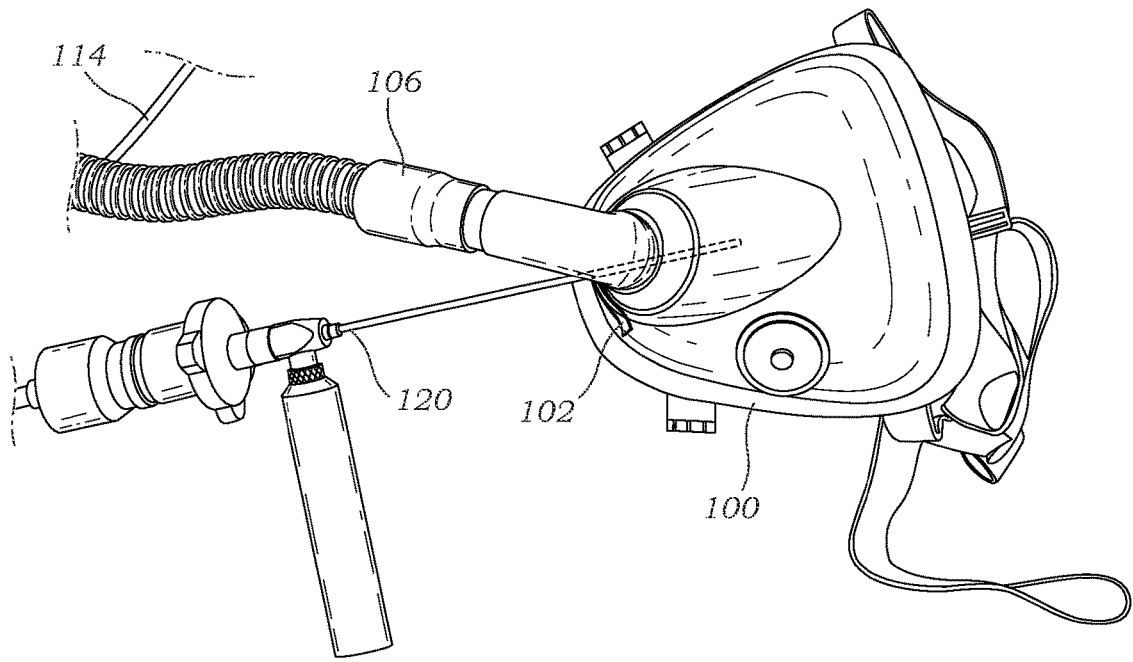

FIGS. 4A-4D illustrate a device for quantifying nasal valve collapse in accordance with some embodiments. FIG. 4A shows the full face mask 100 with an exhale valve 104 and a port for receiving an endoscope 102. The exhale valve can be engaged with a tube 106 such that the exhale valve is in fluid communication with the flow sensor 108 (FIG. 4B). The port 104 for receiving the endoscope can form a seal with the endoscope to minimize air flow across the seal when the endoscope passes through the port. FIG. 4B also shows a portion of the system including the tube 106, a flow sensor 108, power source 110, and a data acquisition module 112. FIG. 4C illustrates a view of the endoscope 120 passing through the port 102 on the mask 100. FIG. 4D illustrates the mask 100 and endoscope 120. The endoscope 120 includes optics for obtaining an image of the anatomy along with an endoscopic camera for recording the image of the anatomy and transmitting the image to the data acquisition module 112. The data acquisition module 112 can receive the air flow data from the flow sensor 108 along with any images or video captured by the camera on the endoscope. Data from the endoscope can be provided to the data acquisition module 112 through a cable 114, such as a USB cable. In some cases the data transmission can be done wirelessly.

The data acquisition module 112 can time sync the endoscopic images with the flow meter data from the flow sensor 108. For example, the data acquisition module 112 can assign time stamps to the air flow data and the image frames from the endoscopic camera and synchronize the air flow data and the image frames. The flow sensor 108 can sample the air flow at a higher frequency than the frequency of the images of the taken by the endoscopic camera. For example the air flow data can be measured with a frequency in the neighborhood of KHZ, e.g. on the order of a thousand times a second. In contrast, the endoscopic camera typically captures images on the order of 30-60 frames per second. The data acquisition module 112 can synchronize the time stamps for the images and the air flow data and provide the synchronized images and air flow data to the user, such as the doctor examining and/or treating the patient.

The data acquisition module 112 can include a processor to analyze the received data as described herein. The data acquisition module 112 can communicate with an external computing device, such as a hand held computer, where the images and data can be displayed in real time or manipulated by the user after the data is collected. A companion application, such as a tablet or smartphone application, can be provided with the device to facilitate the collection and analysis of the patient data. An example of a graphical user interface (GUI) is shown in FIGS. 5A-6B that can be used with the external computing device or the companion application.

The air flow sensor 108 can measure air flow rates that are typically generated by a human. For example, in some embodiments the air flow sensor is capable of measuring air flow rates of about 0 liters per minute up to about 100 liters per minute.

The device enables the physician to advise the patient to breathe with a target amount of inspiratory flow for consistent measurements. The physician can provide instructions to the user to modify the inspiratory or inhalation flow rate to meet a desired or pre-determined level. Typically, the physician can instruct the patient to breathe at several different levels, for example, the patient can be instructed to breathe in with a low breath, medium breath, and high breath. Measuring the nasal valve collapse at several different air flow rates allows the physician to quantify and observe the nasal valve collapse at different air flow rates. The different measurements also allow for a plot of the collapse versus air flow rate to be determined as described in detail below. Typically, the correlation of the collapse versus air flow rate corresponds to a substantially linear relationship. The slope of the plot corresponds to the spring constant for the patient anatomy.

The system also allows the physician to observe the amount of nasal valve collapse simultaneously with measuring the air flow passing through the nasal valve. Observing the nasal valve and the movement of the lateral wall during breathing also allows the physician to get additional information about the patient anatomy to improve diagnosis of the issues that the patient may be experiencing. There are several different causes of nasal obstruction. Thus if the physician observes the nasal valve during inspiration and the lateral wall does not significantly collapse then the physician can learn that the patient is less likely to benefit from a nasal implant like the Latera® implant and can further explore additional causes of nasal obstruction. The physician can also observe the size of the nasal valve of the patient, such as whether the patient has a wide open nasal valve, or a statically narrow nasal valve. The physician can also directly observe the flexibility of the lateral wall. Thus, if the patient has a flexible lateral wall and a large nasal valve then nasal valve collapse is less likely to be a problem. In contrast, if the patient has a flexible lateral wall and a narrow nasal valve then nasal valve collapse is more likely to be a problem that can impact breathing.

In some cases the physician can tell from the plot of air flow rate versus time whether the patient is experiencing substantial nasal valve collapse. For example, if the plot of the air flow rate during inhalation initially goes up and then sharply decreases to a lower plateau then it is likely that the nasal valve collapsed with the initial inhalation to restrict the air flow rate to the lower plateau value.

Figure 5A:
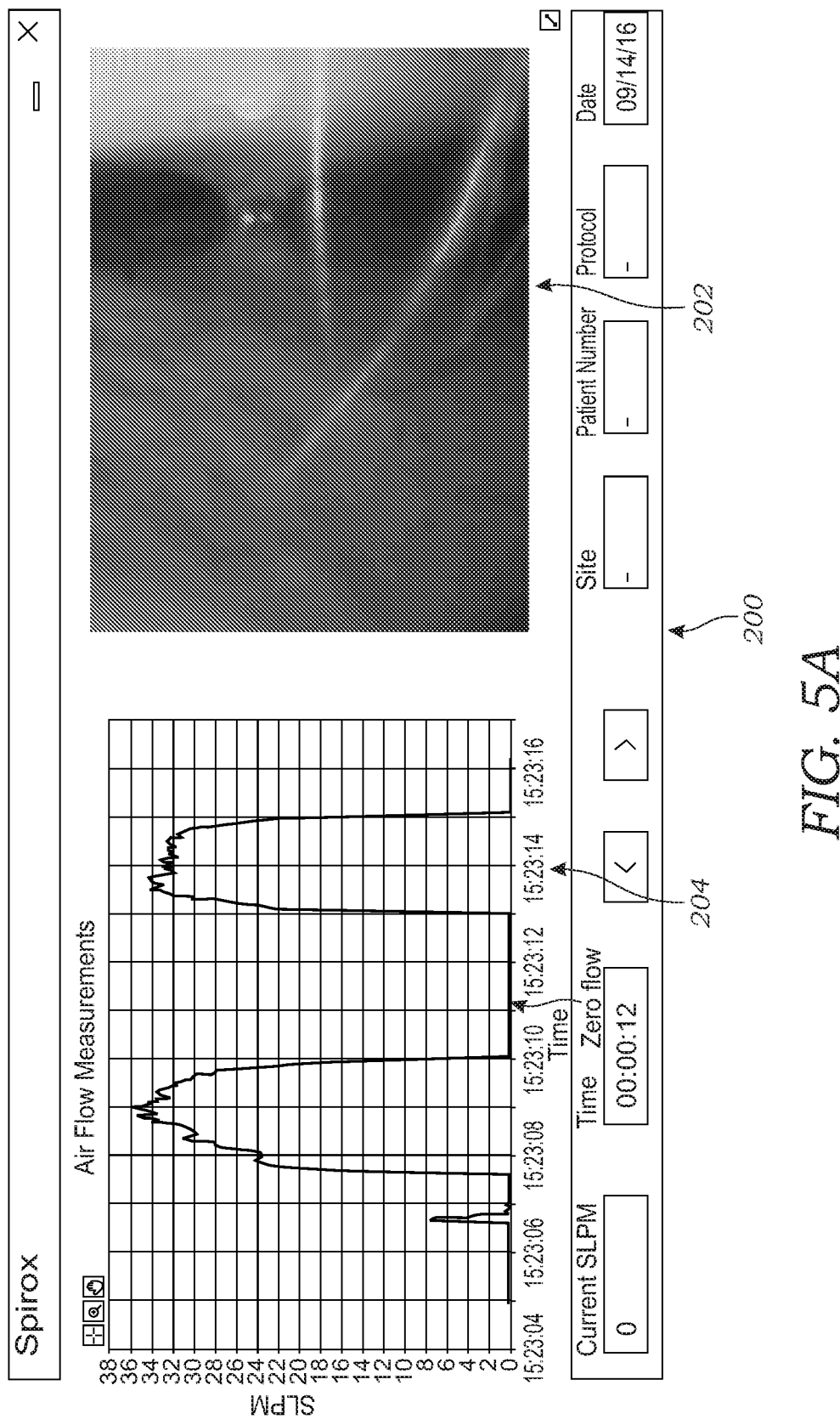
FIGS. 5A-5B illustrate an example of a graphical user interface (GUI) that can be used with methods for quantifying the nasal valve collapse in accordance with some embodiments.
Figure 5B:
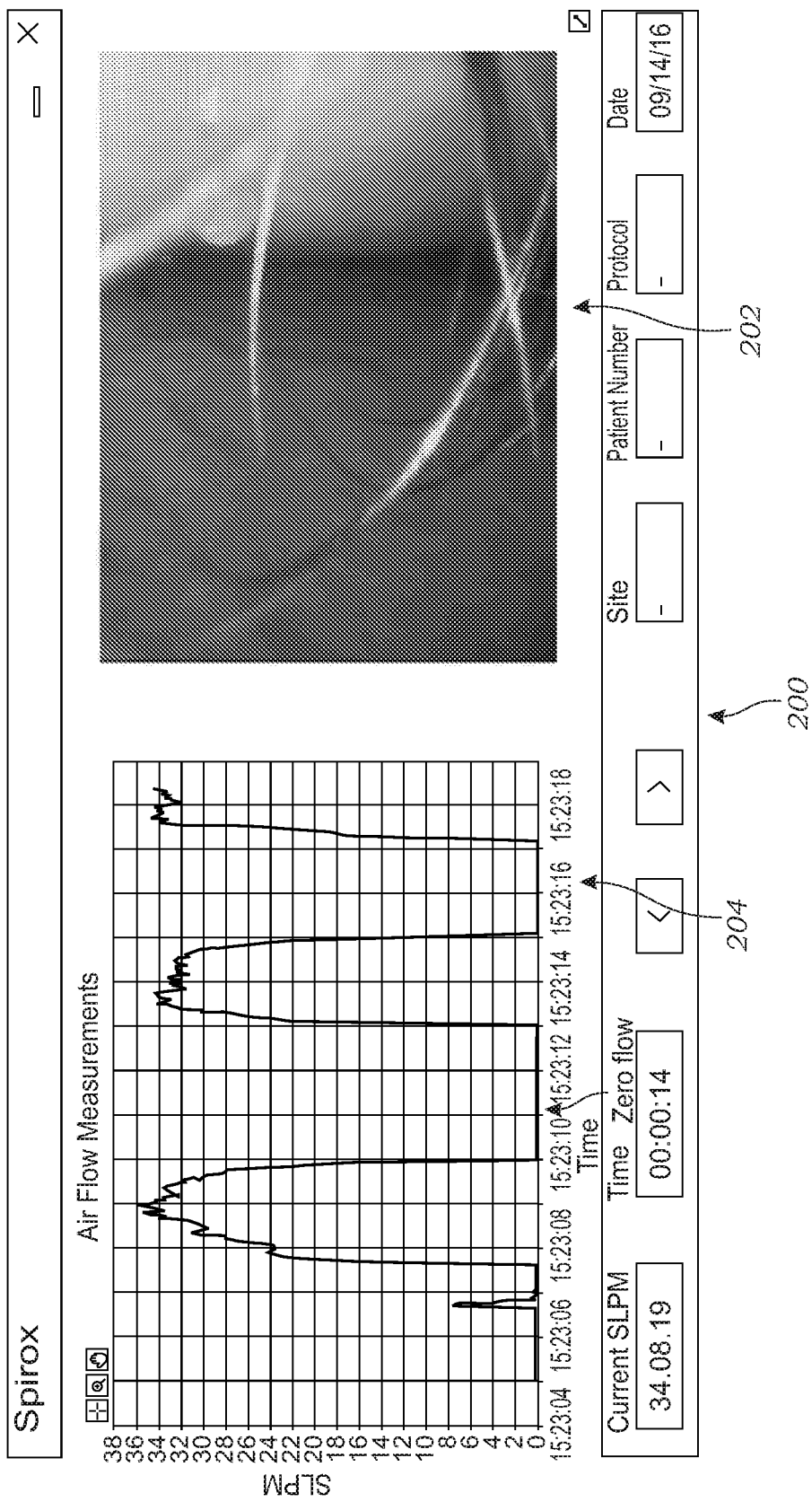

FIG. 5A-5B illustrates an example of a method for quantifying the nasal valve collapse in accordance with some embodiments. The graphical user interface (GUI) 200 illustrated in FIGS. 5A-5B can be displayed on a computer screen, tablet computer, smart phone, or other computer device with a display. FIG. 5A illustrates a GUI 200 with an image 202 of the lateral wall and nasal valve captured by the camera on the endoscope along with air flow measurements 204 of the inhalation rate of the user captured by the air flow sensors of the diagnostic tool. The air flow rates are shown in standard liters per minute (SLM) versus time. FIG. 5B shows a similar GUI 200 as FIG. 5A but the image of the nasal valve 202 shows the nasal lateral wall collapsed during inhalation.

Still frames from a video captured by the endoscopic camera can be selected based on the corresponding flow rates for both the non-inspiring baseline image, and the image at the desired inspiratory flow rate.

The software, on the device or operated by a remote computer, then enables a linear measurement to be obtained for both baseline and inspiratory images and these measurements are then used to calculate a percentage reduction in distance between septum and lateral wall due to nasal valve collapse.

The device and methods output a high resolution measurement of lateral wall collapse at a specific air flow rate. In contrast to some prior art techniques the output is a quantitative measurement of the nasal valve collapse. The use of the full face mask can prevent modifying the properties of the nasal lateral wall to further improve the usefulness of the diagnostic tool and associated methods. The present disclosure allows for a significant improvement in diagnostics of degree of nasal valve collapse and objective measurement of the changes in the ability of the lateral wall to resist collapse after surgical correction thus enabling comparison of the various surgical correction methods.

Figure 6A:
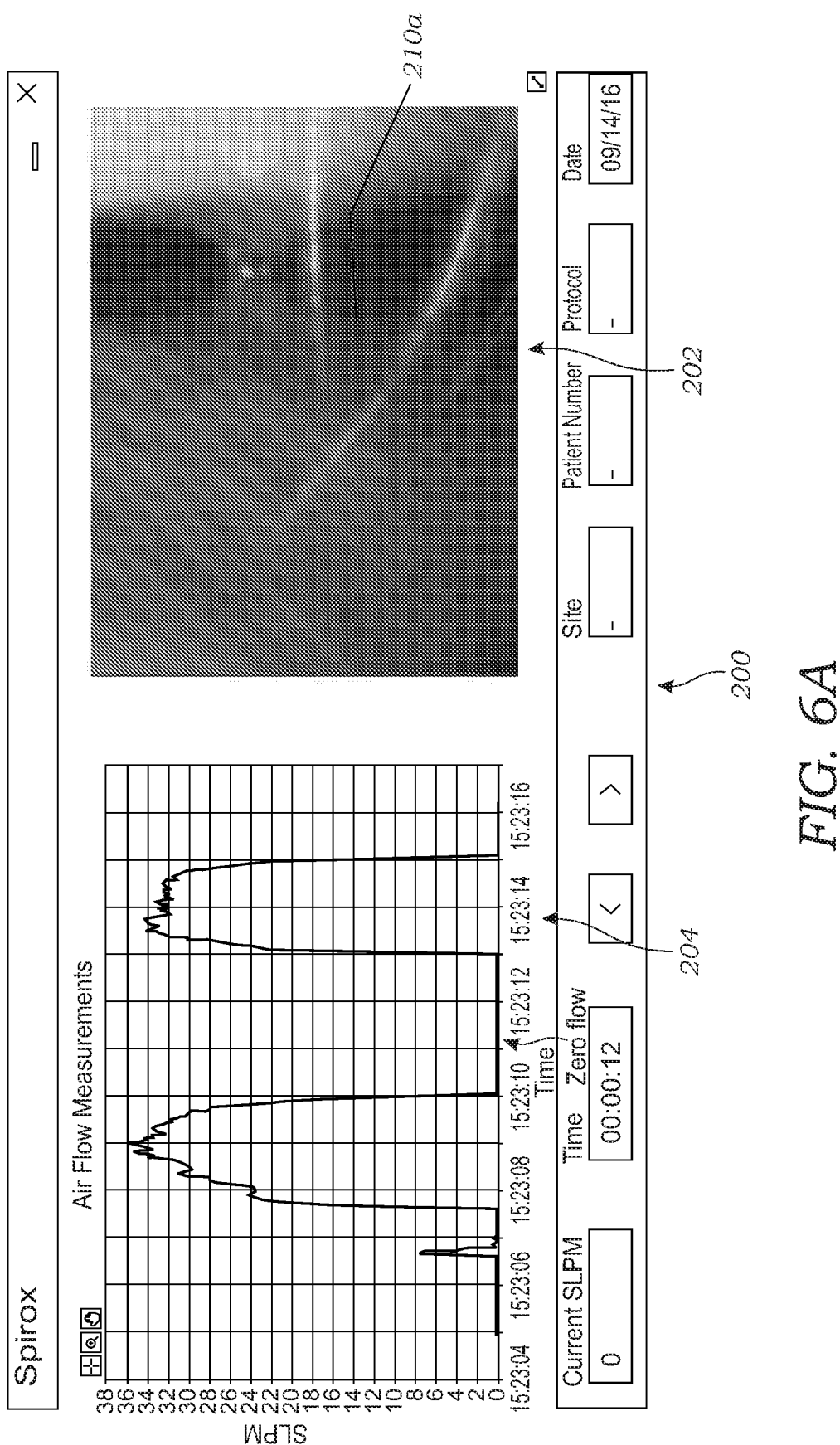
FIGS. 6A-6B illustrate an example of a graphical user interface (GUI) that can be used with methods for quantifying the nasal valve collapse in accordance with some embodiments.
Figure 6B:
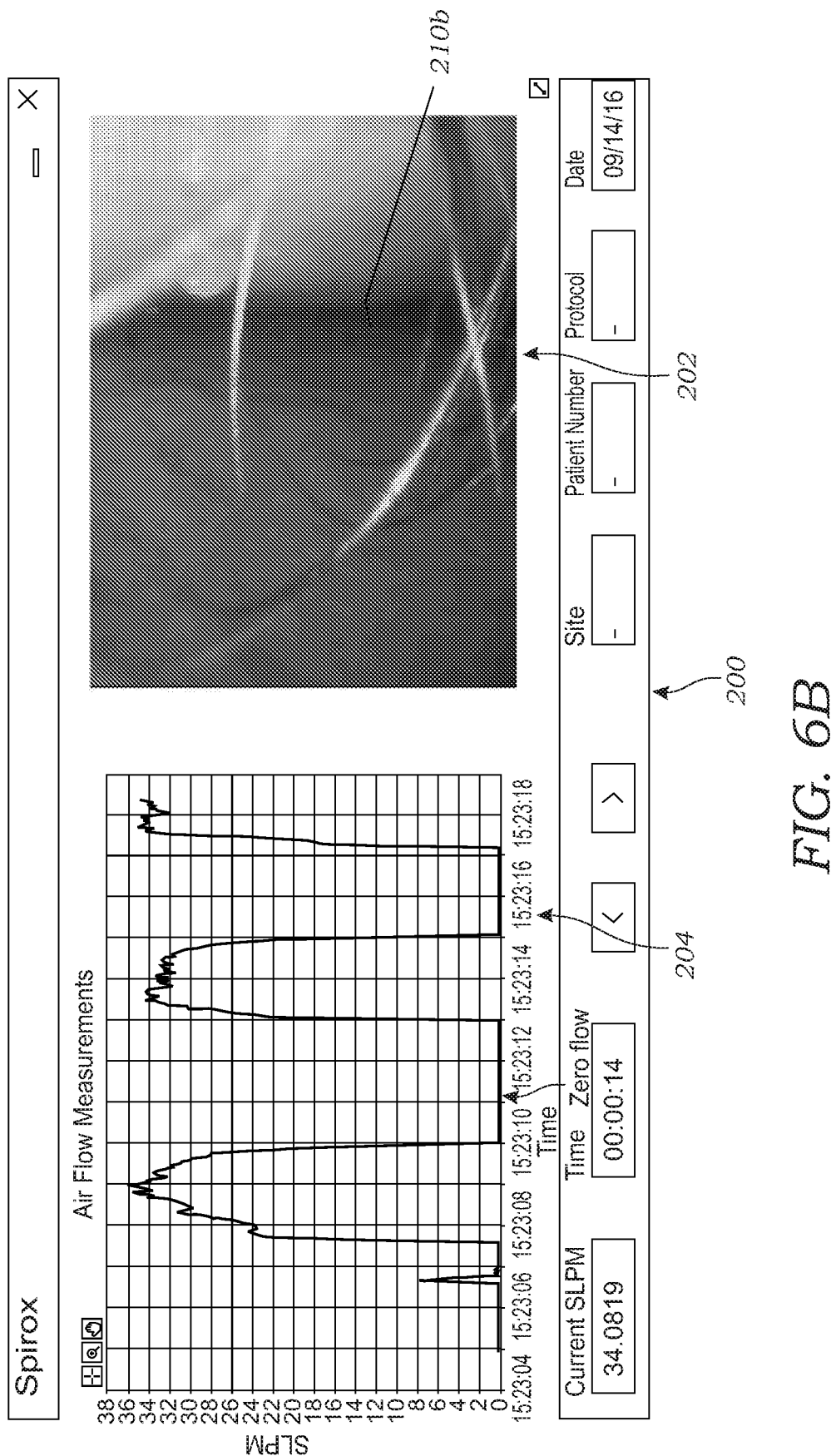

FIGS. 6A-6B illustrate how the physician or other user of the application can review and annotate the collected data with the GUI 200. The GUI 200 allows the physician or other user to pick a point on the timeline showing the air flow measurements and the corresponding image 202 of the septum and lateral wall is displayed. The user can draw a line 210a, 210b to indicate the distance between the lateral wall and the septum. The line 210a shows the distance between the lateral wall and the septum with the GUI 200 showing the air flow in SLPM as zero (e.g. zero flow). The line 210b shows the distance between the lateral wall and the septum with the GUI 200 showing the air flow of 34.08 SLPM. The extent of the collapse can be determined by dividing the length of line 210b/210a. In some cases the length of the lines 210a/210b that are drawn can be determined by counting the pixels in the line.

In some embodiments the user could trace the perimeter of the nasal valve (e.g. septum and lateral wall) and the program can calculate the relative area contained in the nasal valve. In some cases the methods can include applying image analysis techniques to measure the area of the space between the septum and lateral wall to automatically determine the area or length between the septum and lateral wall at zero flow and at another flow rate followed by calculating the percentage difference between the two measurements.

The physician or user can select the specific time and corresponding air flow and images of nasal anatomy to observe using the GUI 200. In some cases the physician uses their knowledge and expertise to choose the specific points used to measure the nasal valve collapse and corresponding air flow rates. In this scenario the system then provides the quantification of the data based on the physician selected times for the measurement. Typically, measurements are not used where there is a steep transition or change in the air flow rate as these areas may result in blurry images or images with poor resolution. A more consistent and flat region of the air flow versus time plot is desirable. In some embodiments the physician selects a zero flow or at rest position to observe the lateral wall in a relaxed state. The physician can observe the lateral wall position at another air flow rate, typically the point of maximum collapse for a given inspiration. For a given inspiration cycle the physician would select a point where the air flow is stable and the curve is at a plateau. The plateau happens when there is flow limiting typically based on the nasal anatomy and air pathway.

In some embodiments the physician instructs the user to take varying inspiration magnitudes such as a small inspiration, medium inspiration, and a large inspiration. The goal is to observe the nasal anatomy at different air flow rates to generate data for plotting nasal valve collapse versus air flow rate as discussed in detail with respect to FIGS. 7A-7B.

The physician can observe the patient for a predetermined number of inspirations or breathing patterns or until a desired amount of data has been received. In some cases it may be possible to obtain enough data on the lateral wall based on a single inspiration observed by the patient. For example if the air flow rate varies enough over the course of the inspiration then enough discrete measurements may be achieved to make a linear plot as described in FIGS. 7A-7B.

In some cases the nasal valve can be observed in a static state to compare the static size to lateral wall configuration in a dynamic state.

In some embodiments the operator of the endoscope can make a marking on the septum and lateral wall to facilitate observing the movement of the lateral wall and make it easier to determine the points at which to measure the nasal valve collapse. Marking the lateral wall and septum can also make it more likely that the distance is accurately measured between the septum and lateral wall. For example, the orientation of the endoscope and flexibility of the lateral wall can make it difficult to compare the relative position of the lateral wall to the septum for a given point in air pathway. It some cases with the flexible lateral wall the user could inadvertently measure the distance between the septum and a point of the lateral wall that is posterior or anterior to the point of the lateral wall. The marking can be done using a pen color that is in the visible spectrum. In some cases the pen can be applied by touching a portion of the endoscope containing the ink such that capillary action causes the ink to flow and mark the surface of the septum/lateral wall.

Figure 7A:
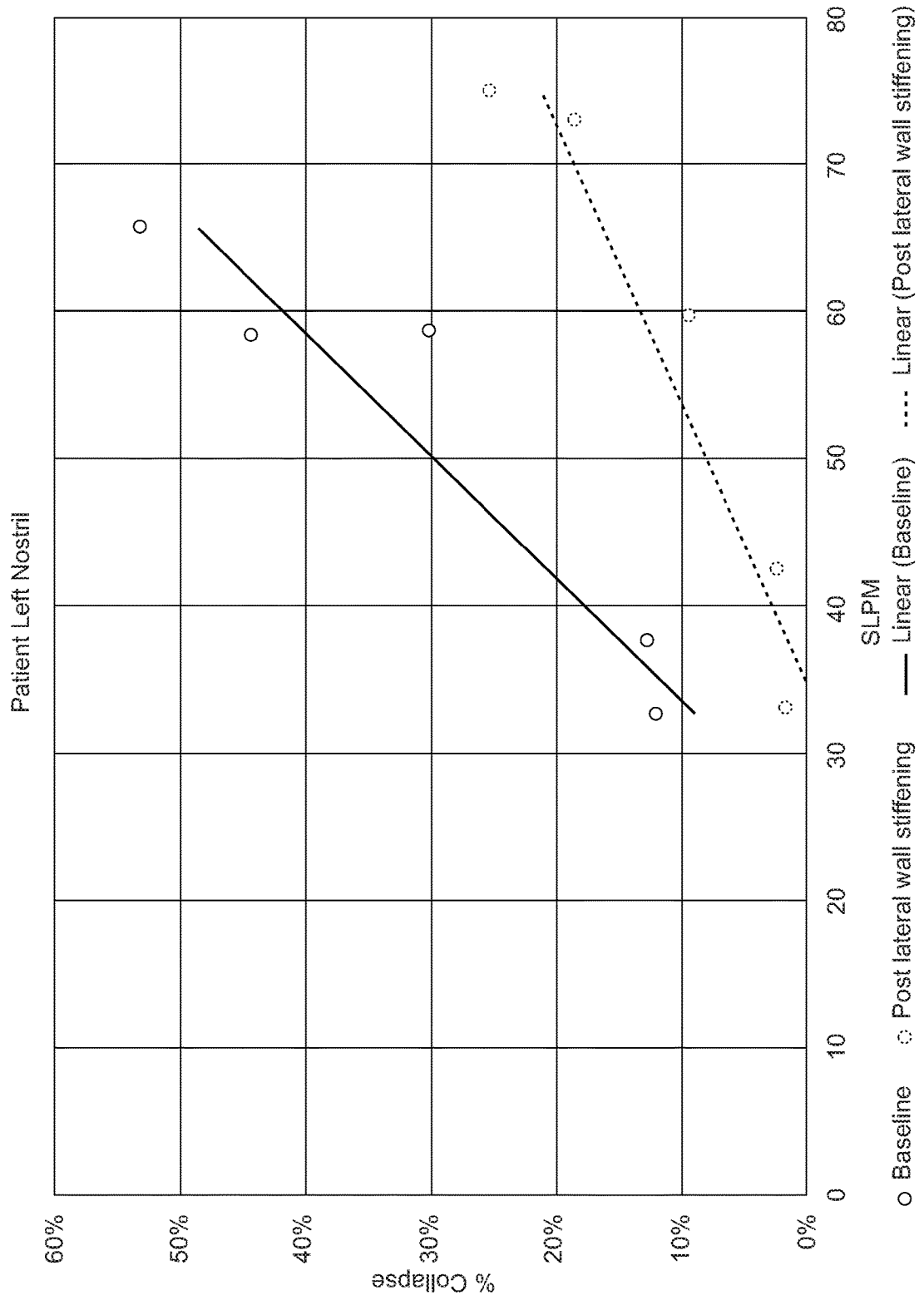
FIGS. 7A-7B illustrate exemplary graphs showing nasal valve collapse versus airflow for a patient's left nostril and right nostril, respectively, in accordance with some embodiments.
Figure 7B:
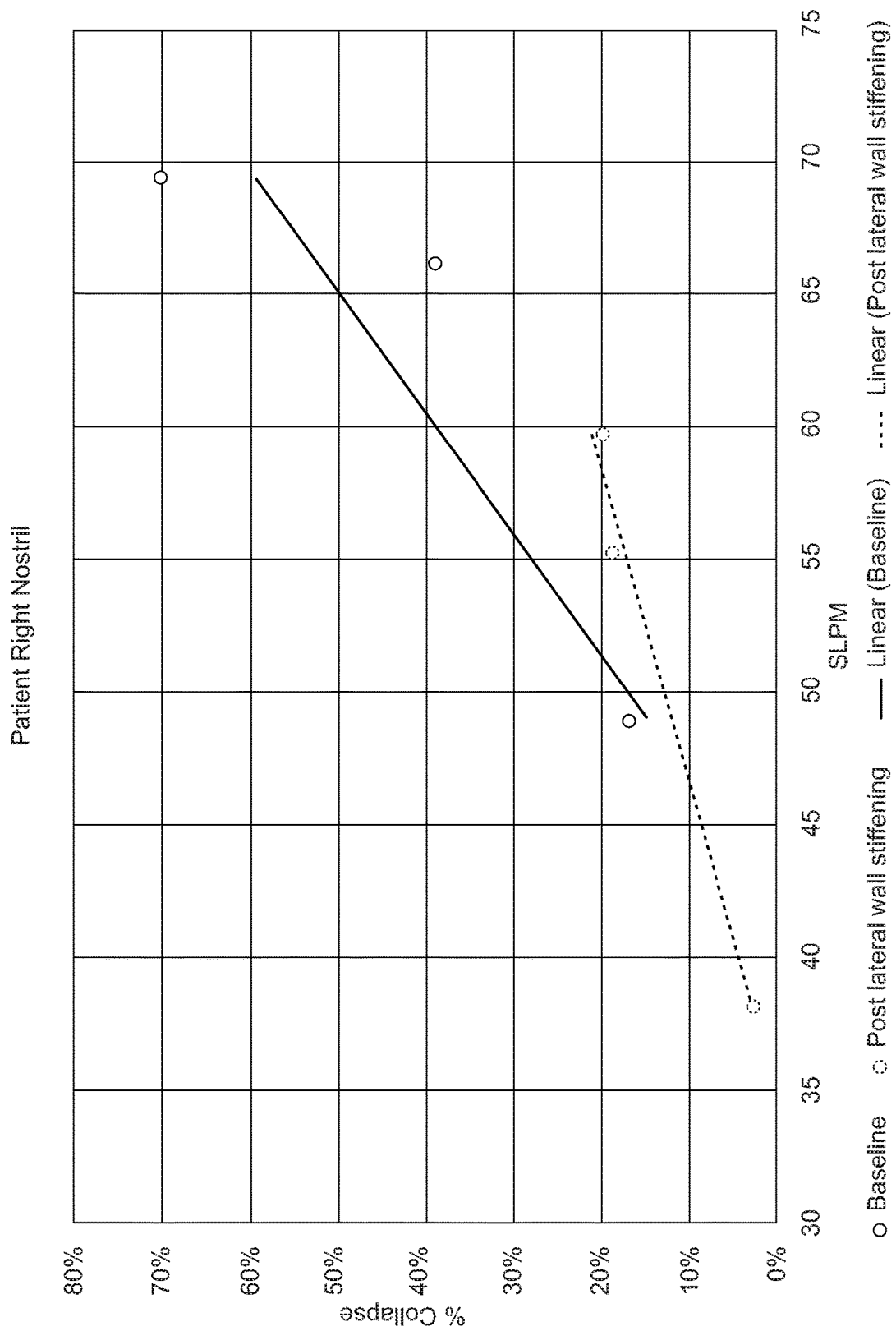
Figure 8A:
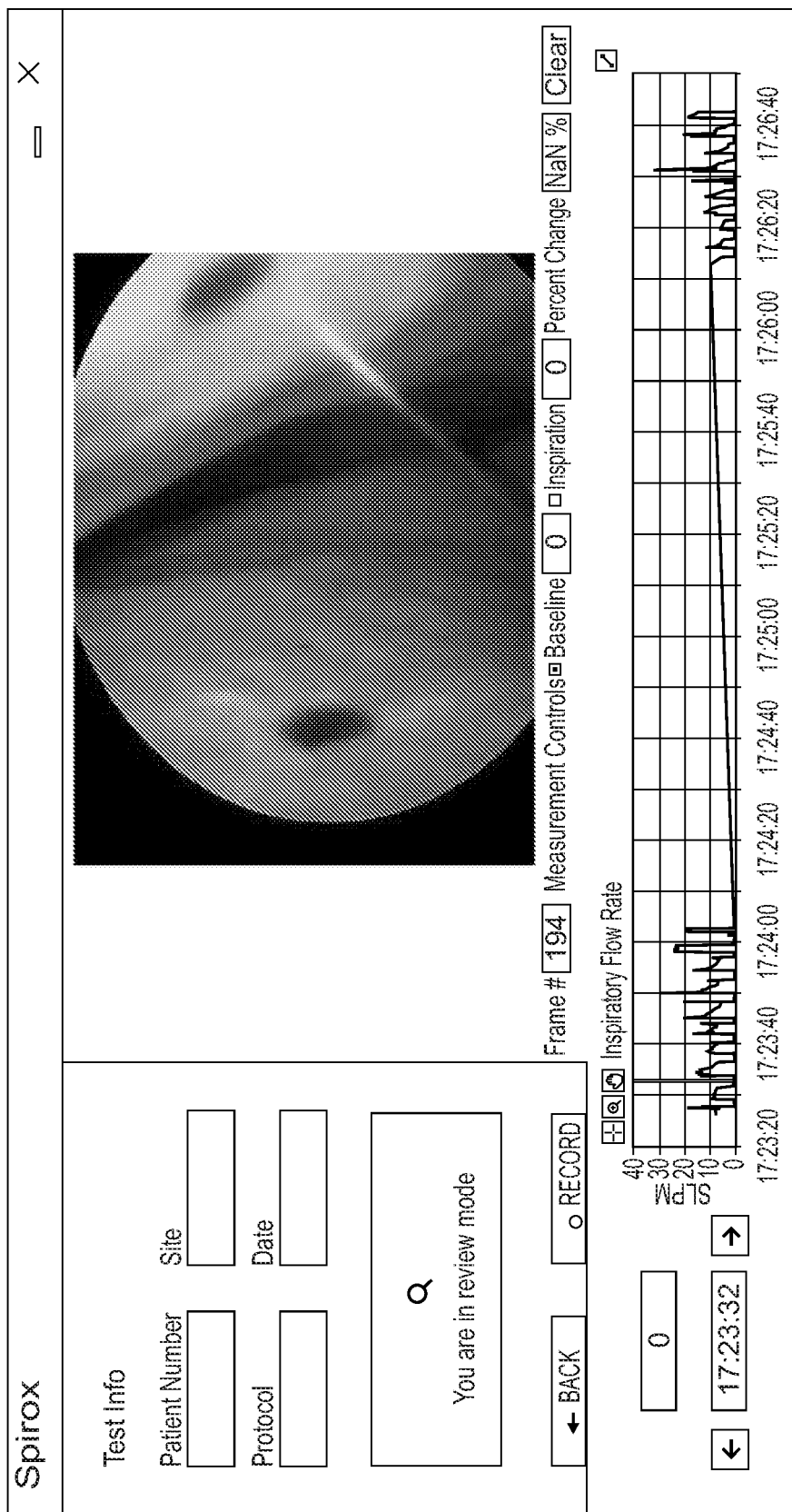
FIGS. 8A-8B illustrate additional examples of a graphical user interface (GUI) that can be used with methods for quantifying the nasal valve collapse in accordance with some embodiments.
Figure 8B:
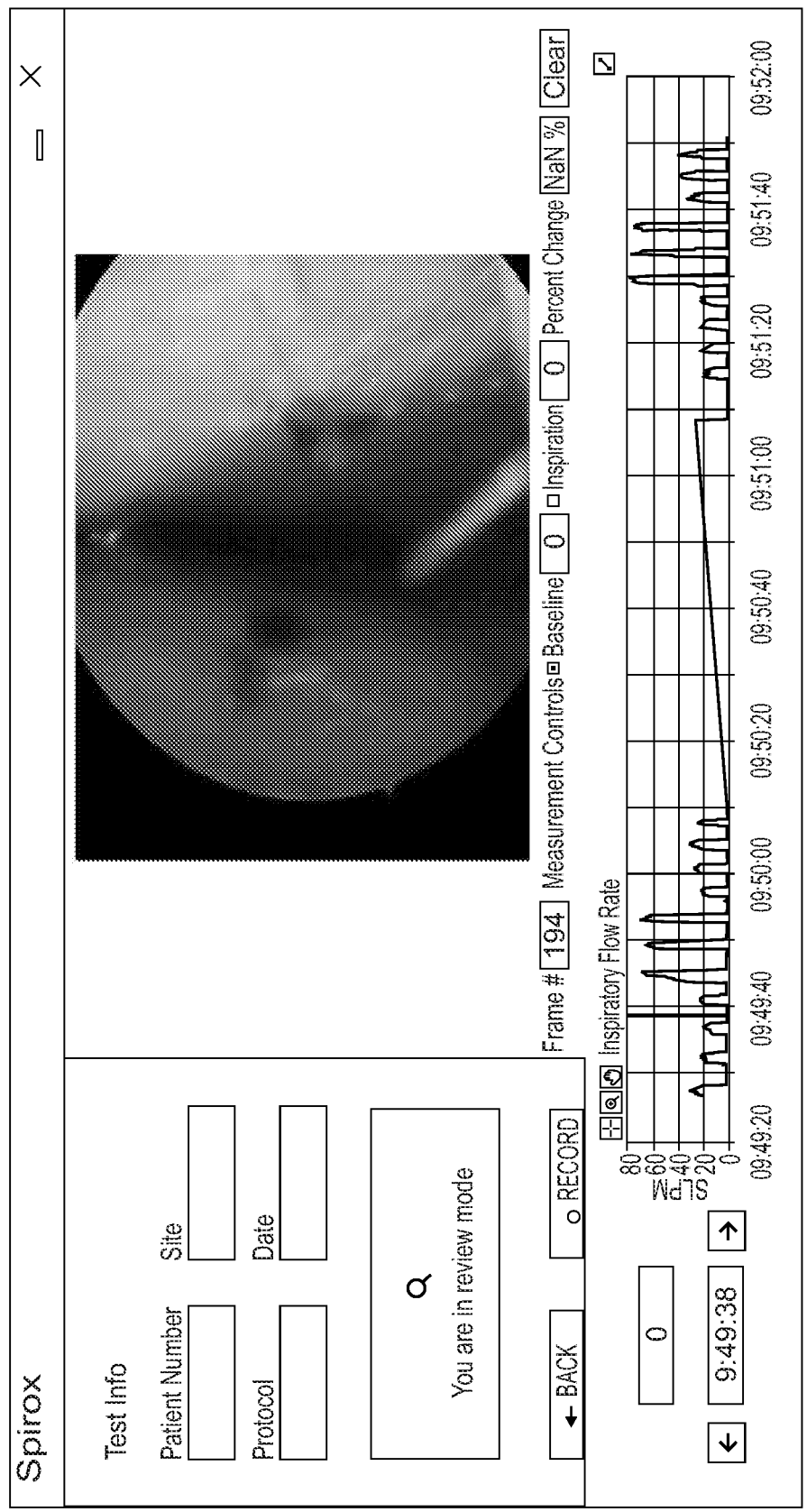

FIGS. 8A-8B illustrate additional examples of a graphical user interface (GUI) that can be used with methods for quantifying the nasal valve collapse in accordance with some embodiments. FIGS. 8A-8B illustrate a review mode for the GUI 300. The GUI 300 shows a variety of information relating to the patient for the physician to review and analyze. The GUI 300 shows patient number, location of the test, test protocol, date, and other information. The GUI 300 indicates that the physician is in review mode. The GUI 300 provides an image of the nasal valve along with specific details of the frame and other related data such as the inspiration level for that particular image. The illustrated image of the nasal valve shows markings on the septum and lateral wall that can be used by the physician to facilitate the determination of the distance between the septum and the lateral wall. The GUI 300 also includes a plot of air flow in SLPM versus time. The plot of air flow in SLPM can be used by the physician to select a specific point in time along the plot such that after the time is selected the corresponding image of the nasal valve is shown to the physician. The GUI 300 provides a toggle or button feature to annotate the image for the nasal valve collapse quantification. The physician can click on the "baseline" or "inspiration" button, as appropriate, followed by annotating the image to draw a line between the septum and the lateral wall. After the GUI 300 has received the baseline and inspiration lines, the nasal valve collapse can be calculated and provided as a percentage as shown on the GUI 300. After several data points have been received by the system a graph of the nasal valve collapse versus airflow can be generated and presented to the user. Example of the graphs are shown in FIGS. 7A-7B.

FIGS. 7A-7B illustrate examples of graphs of nasal valve collapse versus airflow in standard liters per minute (SLPM) obtained using the systems and methods described herein. For many patients the nasal valve collapse versus air flow rate has a substantially linear relationship with the slope of the line corresponding to the spring constant for the lateral wall. FIG. 7A shows the collapse for the patient's left nostril before and after providing an implant to stiffen the lateral wall. The before and after plots are each based on five data points with the dotted lines corresponding to a linear fit of the data points. The graph in FIG. 7A clearly shows the improvement of the implant that is used to stiffen the lateral wall with the significantly flatter slope of the fit line along with the overall lower collapse values post lateral wall stiffening. FIG. 7B shows the collapse for the patient's left nostril before and after providing an implant to stiffen the lateral wall. In FIG. 7B the before and after plots are each based on three data points with the dotted lines corresponding to a linear fit of the data points. The graph in FIG. 7B also clearly shows the improvement of the implant that is used to stiffen the lateral wall with the significantly flatter slope of the fit line along with the overall lower collapse values post lateral wall stiffening.

In some cases the relationship between the air flow rate and nasal valve collapse can have a non-linear relationship. In some embodiments the air flow rate and nasal valve collapse can be modeled using a more complicated equation. For example, more complicated models can be used for patients with significant nasal valve collapse like full collapse or close to full collapse of the nasal valve.

Data for the patients obtained using the system can be aggregated to determine ranges for the spring constant of the lateral wall. The spring constant values can be classified into various categories such as flexible, average, and stiff.

The spring constant value for the patient anatomy can be measured as described herein and considered by the physician treating the patient as one piece of information used to diagnose and treat the breathing issues that the patient may be experiencing. For example, the spring constant of the lateral wall and overall size of the nasal valve can be taken into consideration when developing a treatment plan for the patient. For example, a flexible spring constant of the lateral wall and a small size of the nasal valve may indicate that using a nasal implant to stiffen the nasal valve may be beneficial for the patient. In another example, a stiffer spring constant of the lateral wall and/or a large size of the nasal valve may indicate that the nasal obstruction is primarily due to septum or turbinate related issues. In this scenario using a nasal implant to stiffen the nasal valve may be less likely to benefit the patient.

Figure 9:
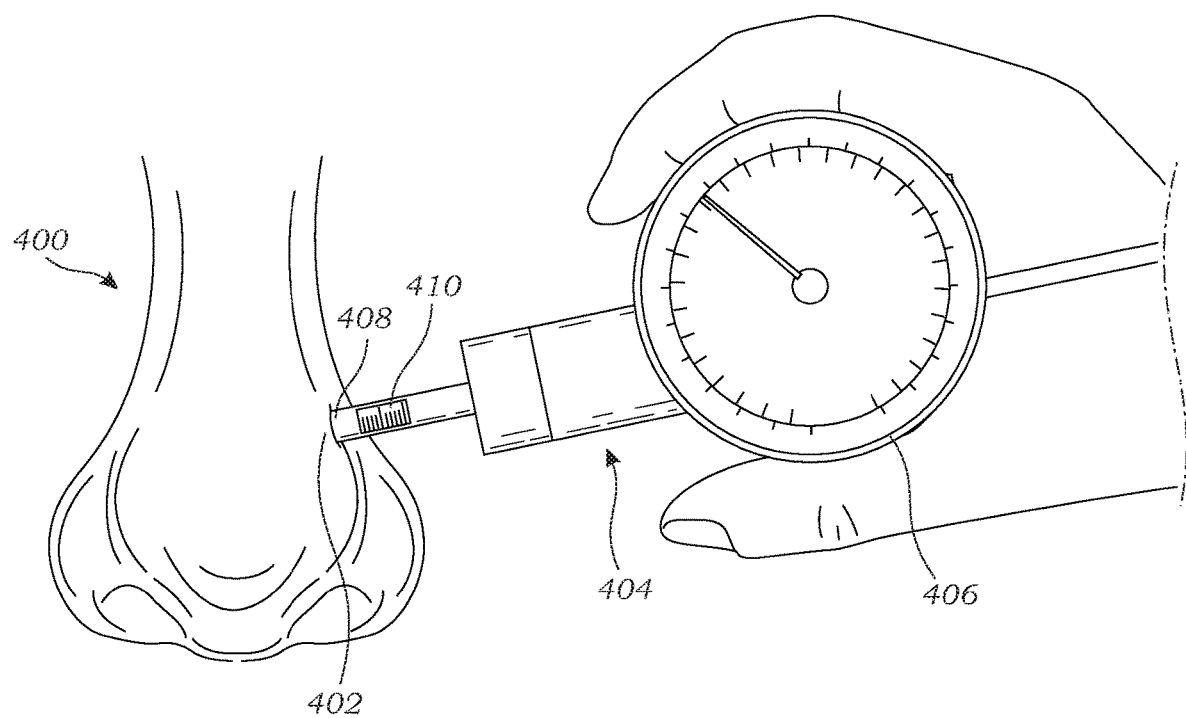
FIG. 9 illustrates a device for measuring the force for deflecting a portion of the nasal lateral wall in accordance with some embodiments.

FIG. 9 illustrates a device that can be used to measure the deflection of the lateral wall 402 of the nose 400 of a patient in accordance with some embodiments. The device 404 includes a plunger 408 that can be pushed against the lateral wall 402 of the nose 400 to measure the force on the force dial 406 for a given deflection. The device 404 can include a ruler 410 or markings such that the force is measured for a desire deflection length. The desired deflection length can be selected based on the physician preferences, configuration of the device 400, patient anatomy, etc. In some embodiments the desired deflection length is 3 mm. There can be a mark on the plunger of the device 404 to show the desired deflection length. The user can record the peak force shown on the force dial 406 when the desire deflection length has been achieved. In some embodiments the desired deflection length can be less than about 10 mm, 9 mm, 8 mm, 7 mm, 6 mm, 5 mm, 4 mm, 3 mm, 2 mm, or 1 mm. The force reading at the desired deflection can be obtained and compared to the spring constant value ranges measured herein. The device 404 can be a quick, easy, and convenient way to get an indication of the properties of the lateral wall of the patient. This piece of information can be useful in the diagnoses and treatment of the patient. In some embodiments the device 404 can optionally include a patient engagement surface that can rest against a portion of the face of the patient to assist with steadying the device and orientation of the device relative to the patient while measuring the force for the desired deflection length.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A system for measuring a nasal valve collapse of a patient comprising:
   a facial mask adapted to form a seal with a facial structure of the patient, the facial mask including an endoscope port and an opening to allow air flow;

an air flow sensor in fluid communication with the opening of the facial mask configured to measure an air flow across the opening;

an endoscope with a camera adapted to pass through the endoscope port in the facial mask and image a nasal valve; and a data acquisition module configured to:

receive a plurality of images from the camera and a plurality of air flow measurements from the air flow sensor, determine (i) a first image of the plurality of images of the nasal valve taken during inhalation and (ii) a second image of the plurality of images of the nasal valve taken during a period between exhalation and inhalation, wherein the second image is determined based on a zero flow measurement of the plurality of air flow measurements, wherein the first image is determined based on a non-zero flow measurement of the plurality of air flow measurements, and determine, based on the first image and the second image, a size difference of the nasal valve during inhalation and during the period between exhalation and inhalation.

2. The system of claim 1, wherein, to determine the size difference of the nasal valve, the data acquisition module is configured to:

determine, based on the first image, a first distance between a septum and a lateral wall of the nasal valve during inhalation, determine, based on the second image, a second distance between the septum and the lateral wall of the nasal valve during the period between exhalation and inhalation, and determine the size difference by dividing the first distance by the second distance.

3. The system of claim 1, wherein the plurality of images are taken during a plurality of inhalation rates, wherein the plurality of inhalation rates are different from each other, and wherein the data acquisition module is further configured to, for each inhalation rate, determine a relative distance between a septum and a lateral wall of the nasal valve.

4. The system of claim 3, further comprising a display device that is configured to display a graph of (i) the relative distances between the septum and the lateral wall of the nasal valve at the plurality of inhalation rates versus (ii) the air flow measurements at the plurality of inhalation rates.

5. The system of claim 1, further comprising a display device configured to display a graphical user interface, GUI.

6. The system of claim 5, wherein the graphical user interface, GUI, is configured to display (i) an image of the plurality of images taken at a first time and (ii) an air flow measurement measured at the first time.

7. The system of claim 5, wherein the data acquisition module is further configured to:

receive an annotation of the first image of the nasal valve during inhalation, wherein the annotation of the first image indicates a distance between a septum and a lateral wall of the nasal valve in the first image;

determine a first distance between the septum and the lateral wall based on the annotation of the first image of the nasal valve during inhalation;

receive an annotation of the second image of the nasal valve during the period between exhalation and inhalation, wherein the annotation of the second image indicates a distance between the septum and the lateral wall of the nasal valve in the second image; and determine a second distance between the septum and the lateral wall based on the annotation of the second image of the nasal valve during the period between exhalation and inhalation; and determine the size difference of the nasal valve based on the first distance and the second distance.

8. The system of claim 7, wherein the graphical user interface, GUI, is configured to display the annotation of the first image and the annotation of the second image.

9. The system of claim 7, wherein the annotation of the first image comprises a line across the nasal valve between the lateral wall and the septum in the first image, and the annotation of the second image comprises a line across the nasal valve between the lateral wall and the septum in the second image.

10. The system of claim 7, wherein the annotation of the first image comprises a tracing of a perimeter of the nasal valve in the first image, and the annotation of the second image comprises a tracing of the perimeter of the nasal valve in the second image.

11. The system of claim 5, wherein the graphical user interface, GUI, is configured to display a graph including the air flow measurements versus time.

12. The system of claim 11, wherein the graphical user interface, GUI, is configured to:

receive an input from a user indicating a time of interest on the graph; and display an image of the plurality of images of the nasal valve that was taken at the time of interest.

13. The system of claim 1, wherein the data acquisition module is configured to apply image analysis to the first image to automatically measure an area of space between a septum and a lateral wall to automatically determine an area or a length of the septum and a lateral wall.

14. The system of claim 1, wherein the camera is configured to capture the plurality of images as a video of the nasal valve.

15. The system of claim 1, wherein the data acquisition module is configured to synchronize the plurality of images from the camera and the plurality of air flow measurements from the air flow sensor using a plurality of time stamps associated with the plurality of images and the plurality of air flow measurements.

16. The system of claim 1, wherein the facial mask is adapted to engage with the facial structure of the patient without changing a nasal anatomy of the patient.

17. The system of claim 1, wherein the data acquisition module is configured to determine the size difference of the nasal valve during inhalation and during the period between exhalation and inhalation by calculating, based on the first image and the second image, a percentage difference in an area or one or more dimensions of the nasal valve between the image of the nasal valve taken during inhalation and the image of the nasal valve during zero flow.

18. The system of claim 1, further comprising an external computing device communicating with the data acquisition module, wherein the external computing device comprises a display having a graphical user interface (GUI) for display of patient data.

19. The system of claim 18, wherein the graphical user interface (GUI) is configured to display a degree of nasal valve collapse simultaneously with air flow passing through the nasal valve.

20. The system of claim 1, wherein the endoscope port is located at a bottom of the facial mask and comprises a sealed port.

\* \* \* \* \*